US006492371B2

(12) United States Patent
Roylance

(10) Patent No.: US 6,492,371 B2
(45) Date of Patent: Dec. 10, 2002

(54) USE OF CYCLIC GMP-SPECIFIC PHOSPHODIESTERASE INHIBITORS FOR TREATMENT OF PARKINSON'S DISEASE

(76) Inventor: H H. Roylance, 6750 SE. Woodward, Portland, OR (US) 97206

( * ) Notice: Subject to any disclaimer, the term of this patent is extended or adjusted under 35 U.S.C. 154(b) by 0 days.

(21) Appl. No.: 09/989,672

(22) Filed: Nov. 21, 2001

(65) Prior Publication Data

US 2002/0077274 A1 Jun. 20, 2002

Related U.S. Application Data

(63) Continuation of application No. 09/836,744, filed on Apr. 17, 2001, now abandoned.
(60) Provisional application No. 60/198,180, filed on Apr. 19, 2000.

(51) Int. Cl.$^7$ ............................................. A61K 31/497
(52) U.S. Cl. .................................................. 514/252.16
(58) Field of Search .................................... 514/252.16

(56) References Cited

U.S. PATENT DOCUMENTS

| | | | |
|---|---|---|---|
| 4,147,789 A | 4/1979 | Stütz et al. | 424/261 |
| 5,702,936 A | 12/1997 | Beavo et al. | 435/196 |
| 5,859,006 A | 1/1999 | Daugan | 514/249 |
| 5,981,527 A | 11/1999 | Daugan et al. | 514/250 |
| 6,001,847 A | 12/1999 | Daugan et al. | 514/287 |
| 6,166,219 A | * 12/2000 | Yamasaki et al. | 548/309.4 |
| 6,251,904 B1 | * 6/2001 | Bunnage et al. | 514/252.6 |

FOREIGN PATENT DOCUMENTS

| | | |
|---|---|---|
| WO | WO 97/43287 | 11/1997 |
| WO | WO 98/53819 | 12/1998 |
| WO | WO 99/21831 | 5/1999 |
| WO | WO 99/24433 | 5/1999 |
| WO | WO 99/26946 | 6/1999 |
| WO | WO 99/28319 | 6/1999 |
| WO | WO 99/28325 | 6/1999 |
| WO | WO 99/31065 | 6/1999 |
| WO | WO 99/42452 | 8/1999 |
| WO | WO 99/54284 | 10/1999 |
| WO | WO 99/54333 | 10/1999 |
| WO | WO 01/32170 | 5/2001 |

OTHER PUBLICATIONS

Calne et al., "Treatment of Parkinsonism with Bromocriptine", *Lancet*, 2:1355–1356 (1974).
Calne, "Clinical Pharmacology of Dopaminergic Effects in Parkinsonism", *Biochemistry and Neurology*, Bradford & Marsden (Eds.) pp. 21–26 (1976).
Casacchia et al., "Therapeutic Use of a Selective cAMP Phosphodiesterase Inhibitor (Rolipram) in Parkinson's Disease", *Pharm Res Commun*, 15(3):329–334 (1983).
Cheng et al., "Relationship Between the Inhibition Constant ($K_1$) and the Concentration of Inhibitor Which Causes 50 Per Cent Inhibition ($I_{50}$) of an Enzymatic Reaction", *Biochem Pharmacology*, 22:3099–3108 (1973).
Cotzias et al., "Apomorphine and Parkinsonism", *Trans Am Neurol Ass*, 97:156 (1972).
Hubble, J.P., "Novel Drugs for Parkinson's Disease", *Med Clinics of North America*, 83(2):525–536 (1999).
Kartzinel et al., "Studies with bromocriptine: III. Concomitant administration of caffeine to patients with idiopathic parkinsonism", *Neurology*, 26:741–743 (1976).
Loughney et al., "Isolation and Characterization of cDNAs Corresponding to Two Human Calcium, Calmodulin–regulated, 3', 5'–Cyclic Nucleotide Phosphodiesterases", *J. Biol. Chem.*, 271:796–806 (1996).
Mena et al., "Neurotoxicity of Levodopa on Catecholamine–Rich Neurons", *Mov Disord*, 7:23 (1992).
Price et al., [25] Expression of Heterologous Proteins in *Saccharomyces cerevisiae* Using the ADH2 Promoter, *Methods in Enzymology*, 185:308–318 (1990).
*Remington's Pharmaceutical Sciences*, 18$^{th}$ Ed. (1990, Mack Publishing Co., Easton, PA 18042) pp. 1435–1712.
Shoulson et al., "Caffeine and the antiparkinsonian response to levodopa or piribedil", *Neurology*, 25:722–724 (1975).
Vakil et al., "Pyrimidyl–Piperonyl–Piperazine (ET 495) in Parkinsonism", *Advan Neurol*, 3:121 (1973).
Wells et al., "Cyclic Nucleotide Phosphodiesterase Activities of Pig Coronary Arteries", *Biochim. Biophys. Acta.*, 384:430 (1975).
Wessel et al., "Selegiline—An overview of its role in the treatment of Parkinson's disease", *Clin Invest*, 70:459 (1992).
Swope and Linda, "Preliminary Report: Use of Sildenafil to Treat Dyskinesias in Patients with Parkinson's Disease", *Neurology*, 54(7), Suppl. 3:S19.006 (2000).

* cited by examiner

*Primary Examiner*—Raymond Henley, III
(74) *Attorney, Agent, or Firm*—Marshall, Gerstein & Borun

(57) ABSTRACT

The present invention relates generally to novel therapeutic methods for treating Parkinson's Disease by administering cyclic GMP-specific phosphodiesterase inhibitor compounds.

15 Claims, No Drawings

USE OF CYCLIC GMP-SPECIFIC PHOSPHODIESTERASE INHIBITORS FOR TREATMENT OF PARKINSON'S DISEASE

This is a continuation of U.S. application Ser. No. 09/836,744, filed Apr. 17, 2001, now abandoned which in turn claims the priority benefit under 35 U.S.C. § 119 of U.S. provisional application Serial No. 60/198,180 filed Apr. 19, 2000.

FIELD OF THE INVENTION

The present invention relates generally to novel therapeutic methods for treating Parkinson's Disease by administering cyclic GMP-specific phosphodiesterase inhibitor compounds.

BACKGROUND OF THE INVENTION

Parkinson's Disease (PD) is a progressive degenerative disorder of the central nervous system (CNS) characterized by tremor and impaired muscular coordination. It is fatal if untreated. PD has been reported to affect approximately one percent of Americans over fifty years of age, but unrecognized early symptoms of the disease may be present in as many as ten percent of those over 60 years of age. The current prediction is that one to one and one-half million persons in the United States may be suffering from PD. The disease may appear at any age, but the risk of developing it increases with age. The occurrence of PD is therefore expected to increase in the next one-half century as the average age of individuals in developed countries progressively increases. For the United States, this phenomenon of population aging is predicted to result in a threefold to fourfold increase in PD frequency or several million persons afflicted with PD.

Like some other CNS degenerative disorders, PD begins insidiously. Persons close to the patient may notice the problem before the patient does. The patient's facial expression may appear depressed or apathetic (masked faces) and their voice may become softer in volume and monotonous in tone. The patient may complain of muscular weakness or stiffness. Involuntary movements, such as tremor or the turning in of a foot (dystonia) may become a problem. These symptoms may be noticed during routine activities or they may be present only at certain times such as when the patient is walking or writing. In the initial stages of PD, many patients do not have movement problems. instead, they may complain of anxiety and difficulty sleeping. However, signs of motor system dysfunction become apparent upon neurologic and physical examination.

The hallmark physical signs of PD are tremor, cogwheel rigidity and bradykinesia. Poor postural reflexes are sometimes included as the fourth hallmark sign. When postural reflexes are inadequate, patients may fall if they are pushed even slightly forward or backward, or if they are standing in a moving vehicle such as a bus or train. In PD, tremor typically occurs at rest but may also be present when the arms are raised (postural tremor). Cogwheel rigidity refers to increased tone that is felt by the examiner as a ratchet-like resistance during passive range of motion. Bradykinesia means slowed nonvolitional and/or volitional movements. The masked faces of PD are an example of slowed nonvolitional movement.

The mean duration of PD is about fourteen years. However, without treatment, the period between presentation of clinical features and death is reduced to about nine years. The rate of disease progression is believed to be directly correlated to the rate of neuron loss.

Symptomatic therapies are the most common form of treatment for PD. These remedies attempt to fulfill the basic dictate of traditional medicine, to relieve suffering. These drugs are designed to be used as either monotherapy or adjunctive symptomatic therapy but have little, if any, beneficial effects on underlying disease cause or pathogenesis. The symptomatic compounds can be divided into two groups on the basis of their pharmacologic action—dopaminergic drugs and nondopaminergic drugs.

Most symptomatic PD drugs attempt to replenish, mimic, or enhance the effects of brain dopamine, a neurotransmitter, because PD is thought to be due to defective dopaminergic transmission in the substantia nigra of the basal ganglia. Dopamine itself is neither well absorbed in the gastrointestinal tract nor effectively transported across the blood-brain barrier. L-dopa is dopamine precursor therapy. L-dopa crosses the blood-brain barrier penetrating into the brain, where it is converted to dopamine via the enzyme dopa decarboxylase. L-dopa has poor bioavailability and a short half-life when administered as monotherapy. Less than 1% of orally administered L-dopa penetrates into brain because of rapid peripheral metabolism by the enzymes dopa decarboxylase and catechol-O-methyl transferase (COMT). To improve its bioavailability, L-dopa is formulated with a decarboxylase inhibitor. In the United States, the decarboxylase inhibitor carbidopa is contained in virtually all L-dopa products prescribed during the last 20 years. For the past three decades, L-dopa has served as the mainstay of PD therapy. However, long term treatment with L-dopa often results in disabling complications. Many patients develop unsustained or unpredictable responses to L-dopa along with drug-induced involuntary movements. It has even been postulated by Mena, et al., *Mov Disord* 7:23 (1992), that L-dopa may be neurotoxic and thereby accelerates nigral neuronal degeneration.

Because of the disadvantages of long term L-dopa use, dopamine agonists have been developed for use as monotherapy in early PD to postpone the need to initiate L-dopa therapy and for use as adjunctive therapy later in the disease to permit reduction of L-dopa dosing or enhancement of beneficial dopaminergic effects. Agonists directly stimulate dopamine receptors within the brain, and thus their action is independent of L-dopa.

The first two dopaminergic agonists to be studied, apomorphine, Cotzias, et al., *Trans Am Neurol Ass* 97:156 (1972), and pirebedil, Vakil, et al., *Advan Neurol* 3:121 (1973) have since been abandoned because of adverse side effects. Bromocriptine is an ergot derivative, dopamine agonist that has been found to be effective for the treatment of PD as described by Calne, et al., *Lancet* 2:1355–1356 (1974). In 1997, three new dopamine agonists were added to the armamentarium against PD: carbergoline and two non-ergoline drugs, pramipexole and ropinirole. Interest in the use of dopamine agonists for treatment of PD continues to be high and several other such agonists are currently being tested in clinical trials.

Blockade of other metabolic enzymatic pathways can also be used to enhance the effects of L-dopa or to maintain brain dopamine levels. One of the central metabolic pathways for dopamine is mediated via the enzyme monoamine oxidase type B (MAOB). Wessel, et al., *Clin Invest* 70:459 (1992) demonstrated that the drug selegiline inhibits MAOB and is approved in the United States as adjunctive antiparkinson therapy to be used in conjunction with L-dopa. Another MAOB inhibitor, lazabemide, was initially tested as adjunctive therapy in PD, but it is not being actively developed at this time. Hubble, J P, *Med Clinics of North America*

83(2):525–536 (1999). The compound rasagiline also inhibits the oxidative monoamine metabolic enzymes. Rasagiline's effects in early untreated PD are being investigated. Hubble, supra.

Another enzymatic pathway involves cyclic nucleotide phosphodiesterases. Cyclic nucleotide phosphodiesterases (PDEs) are essential regulators of cyclic nucleotide-dependent signal transduction processes. They terminate the action of the second messengers adenosine 3',5'-cyclic monophosphate (CAMP) and guanosine 3',5'-cyclic monophosphate (cGMP) by hydrolyzing them to their respective 5'-nucleoside monophosphates. Based on their biological properties, the PDEs may be classified into several general families. For example, $Ca^{2+}$/calmodulin-stimulated PDE (Type I), cGMP-stimulated PDE (Type II), cGMP-inhibited PDE (Type III), cAMP-specific PDE (Type IV), cGMP-specific PDE (Type V), and cGMP-specific photoreceptor PDE (Type VI).

The combination of dopamine agonists with phosphodiesterase inhibitors was examined after it was discovered that the striatal dopaminergic receptor was closely associated with an adenylate cyclase. The actions of dopamine are mediated by an adenylate cyclase which produces cyclic AMP. Therefore, patients suffering from PD may be helped by the administration of a phosphodiesterase inhibitor which obstructs the degradation of cAMP as described by Calne, D B in *Biochemistry and Neurology*, Bradford & Marsden (Eds.) pp. 21–26 (1976).

For example, caffeine is known to non-selectively inhibit the action of a cyclic 3',5'-nucleotide phosphodiesterase known to hydrolyze cAMP. However, as described by Kartzinel, et al., *Neurology* 26:741–743 (1976) concomitant administration of caffeine and bromocriptine to patients with PD failed to potentiate the anti-parkinson action of bromocriptine. In addition, Shoulson, et al., *Neurology* 25:722–724 (1975) demonstrated similar results when caffeine was administered in combination with levodopa or piribedil.

U.S. Pat. No. 4,147,789 discloses the combination of 6-methyl-8-thiomethyl-ergolene derivatives with nonselective phosphodiesterase inhibitors for treatment of PD. U.S. Pat. No. 4,147,789 does not disclose using specific phosphodiesterase inhibitors nor does it disclose combining L-dopa with phosphodiesterase inhibitors.

Casacchia, et al., *Pharm Res Commun* 15(3):329–334 (1983), investigated whether a selective cAMP phosphodiesterase inhibitor, rolipram, would improve the effectiveness of L-dopa and dopaminergic ergot derivatives in the therapy of PD. Rolipram failed to potentiate the effect of L-dopa and lisuride.

SUMMARY OF THE INVENTION

The present invention provides novel therapeutic uses for Type V PDE inhibitors in patients suffering from PD. The invention provides methods of preventing and/or slowing the progression of PD or reducing or eliminating clinical symptoms of PD by administering a therapeutically effective amount of one or more Type V PDE (PDE5) inhibitor(s) of the invention. As used herein, a "clinical symptom" of PD includes tremor, cogwheel rigidity, bradykinesia, poor postural reflexes, and any other clinically defined physical or mental manifestation of PD.

The term "$IC_{50}$" is defined as the concentration of a compound that results in 50% enzyme inhibition, in a single dose response experiment. The $IC_{50}$ value therefore is a measure of the potency of a compound to inhibit PDEs, including PDE5. Determining the $IC_{50}$ value of a compound is readily carried out by a known in vitro methodology generally described in Cheng et al., *Biochem Pharmacology* 22:3099–3108 (1973).

The term "inhibiting" or "inhibits" refers to blocking the enzymatic activity of PDE5 to a sufficient degree to reduce a clinical symptom of PD or to prevent the recurrence of a clinical symptom of PD.

The term "a pharmaceutically effective amount" represents an amount of a compound that is capable of inhibiting PDE5, and causes an improvement in a clinical symptom of PD and/or prevents or reduces recurrence of the symptom.

The term "PDE5 inhibitor" refers to a compound that inhibits PDE5. A PDE5 inhibitor useful in the present invention is a compound that inhibits PDE5 and has an $IC_{50}$ value against human recombinant PDE5 of about 10 nM or less. Preferably, the $IC_{50}$ value of the PDE5 inhibitor is about 5 nM or less, more preferably about 3 nM or less, and most preferably about 1 nM or less. Most preferred PDE5 inhibitors are selective PDE5 inhibitors, i.e., those that inhibit PDE5, but do not significantly inhibit other PDE enzymes, particularly PDE6 and PDE1c. With respect to selectivity, a preferred PDE5 inhibitor exhibits a PDE6/PDE5 and a PDE1c/PDE5 $IC_{50}$ inhibition quotient of at least 200, and can range to 1,000 or greater. The PDE6/PDE5 $IC_{50}$ inhibition quotient is the ratio of the $IC_{50}$ value of a compound vs PDE6 to the $IC_{50}$ value of the same compound vs PDE5. The PDE1c/PDE5 inhibition quotient is identically defined for PDE1c and PDE5. To achieve the full advantage of the present invention, the compound has a PDE6/PDE5 and a PDE1c/PDE5 $IC_{50}$ inhibition quotient of at least 100 and an $IC_{50}$ for PDE5 of about 5 nM or less, e.g., about 0.1 to about 5 nM. Therefore, for preferred inhibitors, the $IC_{50}$ value of the PDE5 inhibitor is about 100 times less than the $IC_{50}$ value against PDE6 or PDE1c, more preferably about 500 times less than the $IC_{50}$ value against PDE6 or PDE1c, and most preferably about 1000 times less than the $IC_{50}$ value against PDE6 or PDE1c.

PDE5 inhibitors useful in the present invention vary significantly in chemical structure and the use of a PDE5 inhibitor in the present method is not dependent on a particular chemical structure. However, preferred compounds having the ability to inhibit PDE5 (although not having the preferred selectivity) include compounds having the structural formula (I):

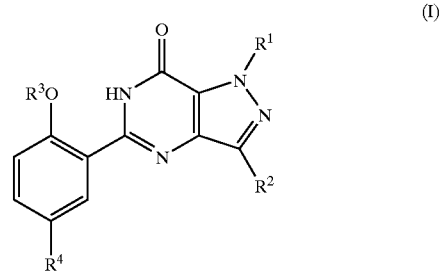

wherein $R^1$ is methyl or ethyl; $R^2$ is n-propyl; $R^3$ is ethyl, n-propyl, or allyl; $R^4$ is $COCH_2NR^5R^6$, $CONR^5R^6$, $SO_2NR^9R^{10}$, or 1-methyl-2-imidazolyl; $R^5$ and $R^6$ together represent, with the nitrogen atom to which they are attached, a morpholino or 4-N($R^{11}$)-piperazinyl group; $R^9$ and $R^{10}$ together with the nitrogen atom to which they are attached represent a 4-N($R^{12}$)-piperazinyl group; $R^{11}$ is methyl or acetyl; and $R^{12}$ is H, methyl, 2-propyl, or 2-hydroxyethyl.

Compounds of structural formula (I), and their preparation, are disclosed in EP 0 702 555, the disclosure of which is incorporated herein by reference. Preferred compounds of formula (I) include;

5-(2-ethoxy-5-morpholinoacetylphenyl)-1-methyl-3-n-propyl-1,6-dihydro-7H-pyrazolo[4,3-d]pyrimidin-7-one;

5-(5-morpholinoacetyl-2-n-propoxyphenyl)-1-methyl-3-n-propyl-1,6-dihydro-7H-pyrazolo[4,3-d]pyrimidin-7-one;

5-(2-ethoxy-5-(4-methyl-1-piperazinylsulphonyl)phenyl)-1-methyl-3-n-propyl-1,6-dihydro-7H-pyrazolo[4,3-d]pyrimidin-7-one;

5-(2-allyloxy-5-(4-methyl-1-piperazinylsulphonyl)phenyl)-1-methyl-3-n-propyl-1,6-dihydro-7H-pyrazolo[4,3-d]pyrimidin-7-one;

5-(2-ethoxy-5-[4-(2-propyl)-1-piperazinylsulphonyl]-phenyl)-1-methyl-3-n-propyl-1,6-dihydro-7H-pyrazolo[4,3-d]pyrimidin-7-one;

5-(2-ethoxy-5-[4-(2-hydroxyethyl)-1-piperazinylsulphonyl]phenyl)-1-methyl-3-n-propyl-1,6-dihydro-7H-pyrazolo[4,3-d]pyrimidin-7-one;

5-(5-[4-(2-hydroxyethyl)-1-piperazinylsulphonyl]2-n-propoxyphenyl)-1-methyl-3-n-propyl-1,6-dihydro-7H-pyrazolo[4,3-d]pyrimidin-7-one;

5-(2-ethoxy-5-(4-methyl-1-piperazinylcarbonyl)phenyl)-1-methyl-3-n-propyl-1,6-dihydro-7H-pyrazolo[4,3-d]pyrimidin-7-one;

5-(2-ethoxy-5-(1-methyl-2-imidazolyl)phenyl)-1-methyl-3-n-propyl-1,6-dihydro-7H-pyrazolo [4,3-d]pyrimidin-7-one; and mixtures thereof.

Another class of preferred compounds is disclosed in Daugan U.S. Pat. No. 5,859,006 and Daugan et al. U.S. Pat. No. 5,981,527, each of which is specifically incorporated herein by reference. This class of compounds, which contains potent and selective PDE5 inhibitors, is useful in treating PD and has the following structural formula (II):

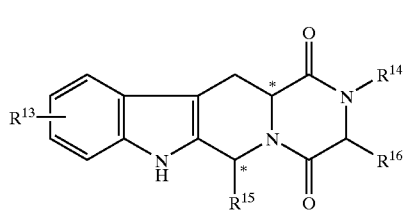

and salts or solvates thereof,
wherein $R^{13}$ is selected from the group consisting of hydrogen, halogen, and $C_{1-6}$alkyl;

$R^{14}$ is selected from the group consisting of hydrogen, $C_{1-6}$alkyl, $C_{2-6}$alkenyl, $C_{2-6}$alkynyl, halo, $C_{3-8}$cycloalkyl, $C_{3-8}$cycloalkyl$C_{1-3}$alky and aryl$C_{1-3}$alkyl, wherein aryl is phenyl or phenyl substituted with one to three substituents independently selected from the group consisting of halogen, $C_{1-6}$alkyl, $C_{1-6}$alkoxy, and methylenedioxy, and heteroaryl$C_{1-3}$alkyl, wherein heteroaryl is thienyl, furyl, or pyridyl, each optionally substituted with one to three substituents independently selected from the group consisting of halogen, $C_{1-6}$alkyl, and $C_{1-6}$alkoxy.

$R^{15}$ represents an optionally substituted monocyclic aromatic ring selected from the group consisting of benzene, thiophene, furan, and pyridine, or an optionally substituted bicyclic ring

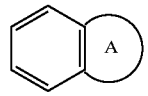

attached to the rest of the molecule via one of the benzene ring carbon atoms, wherein the fused ring A is a 5- or 6-membered ring, saturated or partially or fully unsaturated, and comprises carbon atoms and optionally one or two heteroatoms selected from oxygen, sulphur and nitrogen; and $R^{16}$ represents hydrogen or $C_{1-3}$alkyl, or $R^{14}$ and $R^{16}$ together represent a 3- or 4-membered alkyl or alkenyl chain component of a 5- or 6-membered ring.

Preferred compounds of structural formula (II) are those wherein $R^{13}$ is hydrogen, halogen, or $C_{1-6}$alkyl; $R^{14}$ is hydrogen or $C_{1-6}$alkyl; $R^{15}$ is the bicyclic ring

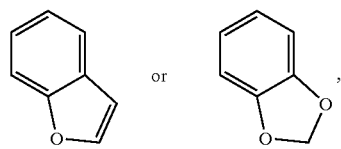

which can be optionally substituted by one or more groups independently selected from halogen and $C_{1-3}$alkyl; and $R^{16}$ is hydrogen or $C_{1-3}$alkyl.

Preferred compounds of structural formula (II) include:

(6R, 12aR)-2,3,6,7,12,12a-hexahydro-6-(5-benzofuranyl)-2-methyl-pyrazino[2',1':6,1]pyrido[3,4-b]indole-1,4-dione;

(6R, 12aR)-2,3,6,7,12,12a-hexahydro-6-(5-benzofuranyl)-pyrazino[2',1':6,1]pyrido [3,4-b]indole-1,4-dione;

(3S, 6R, 12aR)-2,3,6,7,12,12a-hexahydro-6-(5-benzofuranyl)-3-methyl-pyrazino[2',1':6,1]pyrido[3,4-b]indole-1,4-dione;

(3S, 6R, 12aR)-2,3,6,7,12,12a-hexahydro-6-(5-benzofuranyl)-2,3-dimethyl-pyrazino[2'1':6,1]pyrido [3,4-b]indole-1,4-dione;

(6R, 12aR)-2,3,6,7,12,12a-hexahydro-6-(5-benzofuranyl)-2-isopropyl-pyrazino[2',1':6,1]pyrido [3,4-b]indole-1,4-dione;

physiologically acceptable salts and solvates thereof; and mixtures thereof. The compounds of structural formula (II) are particularly advantageous due to their selectivity in inhibiting PDE5 over other PDE enzymes.

Still other exemplary PDE5 inhibitors useful in the present method are those disclosed in Daugan et al. U.S. Pat. No. 6,001,847; WO 97/43287, WO 98/53819, WO 99/21831, WO 99/24433, WO 99/26946, WO 99/28319, WO 99/28325, WO 99/42452, WO 99/54284, WO 99/54333, each incorporated herein by reference.

Further exemplary compounds for use in the present invention are disclosed in PCT application (PCT/EP98/06050), which designates the U.S., entitled "Chemical Compounds," inventors A. Bombrun and F. Gellibert, the disclosure of which is specifically incorporated by reference herein. This class of compounds has the following structural formula (III):

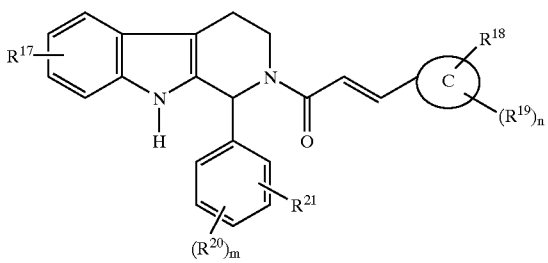

and salts and solvates (e.g., hydrates) wherein
ring C represents a 5- or 6-membered heteroaryl group containing at least one heteroatom selected from the group consisting of oxygen, nitrogen, and sulfur;

$R^{17}$ represents hydrogen or halogen;

$R^{18}$ is selected from the group consisting of hydrogen, nitro ($NO_2$), trifluoromethyl, trifluoromethoxy, halogen, cyano (CN), a 5- or 6-membered heterocyclic group containing at least one heteroatom selected from the group consisting of oxygen, nitrogen, and sulfur, optionally substituted with $C(=O)OR^a$ or $C_{1-4}$alkyl, $C_{1-6}$alkyl, optionally substituted with $OR^h$, $C_{1-3}$alkoxy, $C(=O)R^h$, $OC(=O)OR^h$, $C(=O)OR^h$, $C_{1-4}$alkyleneHet, $C_{1-4}$alkyleneC($=$O)$OR^h$, $OC_{1-4}$alkyleneC($=$O)$OR^h$, $C_{1-4}$alkyleneOC$_{1-4}$alkyleneC($=$O)$OR^h$, $C(=O)NR'SO_2R^j$, $C(=O)C_{1-4}$alkyleneHet, $C_{1-4}$alkyleneNR$^h$R$^i$, $C_{2-6}$alkyleneNR$^h$R$^i$, $C(=O)NR^hR^i$, $C(=O)NR^hR^i$, $C(=O)NR^hC_{1-4}$alkyleneOR$^i$, $C(=O)NR^hC_{1-4}$alkyleneHet, $OR^i$, $OC_{2-4}$alkyleneNR$^h$R$^i$, $OC_{1-4}$alkyleneCH($OR^h$)$CH_2NR^hR^i$, $OC_{1-4}$alkyleneHet, $OC_{2-4}$alkyleneOR$^h$, $OC_{2-4}$alkyleneNR$^h$C($=$O)$OR^i$, $NR^hR^i$, $NR^hC_{1-4}$alkyleneNR$^h$R$^i$, $NR^hC(=O)R^i$, $NR^hC(=O)NR^hR^i$, $N(SO_2C_{1-4}$alkyl)$_2$, $NR^h(SO_2C_{1-4}$alkyl), $SO_2NR^hR^i$, and $OSO_2$trifluoromethyl;

$R^{19}$ is selected from the group consisting of hydrogen, halogen, $OR^h$, $C_{1-6}$alkyl, $NO_2$, and $NR^hR^i$;

or $R^{18}$ and $R^{19}$ are taken together to form a 3- or 4-membered alkylene or alkenylene chain component of a 5- or 6-membered ring, optionally containing at least one heteroatom;

$R^{20}$ is selected from the group consisting of hydrogen, halogen, $NO_2$, trifluoromethoxy, $C_{1-6}$alkyl, $OC_{1-6}$alkyl, and $C(=O)O^h$;

$R^{21}$ is hydrogen, or $R^{20}$ and $R^{21}$ are taken together to form a 3- or 4-membered alkylene or alkenylene chain component of a 5- or 6-membered ring, optionally containing at least one heteroatom;

Het represents a 5- or 6-membered heterocyclic group containing at least one heteroatom selected from the group consisting of oxygen, nitrogen, and sulfur, and is optionally substituted with $C_{1-4}$alkyl;

$R^h$ and $R^i$ can be the same or different, and are independently selected from hydrogen and $C_{1-6}$alkyl;

$R^j$ represents phenyl or $C_{4-6}$cycloalkyl, wherein the phenyl or $C_{4-6}$cycloalkyl can be optionally substituted with one or more halogen atoms, one or more $C(=O)OR^a$, or one or more $OR^h$;

n is an integer 1, 2, or 3; and m is an integer 1 or 2.

In preferred compounds of structural formula (III), C is a heteroaryl group containing at least one nitrogen or sulfur, $R^{19}$ is hydrogen, and $R^{18}$ is selected from the group consisting of $NR^hR^i$ and a 5- or 6-membered heterocyclic group containing at least one nitrogen optionally substituted with $C_{1-4}$ alkyl.

It is contemplated that the PDE5 inhibitors may be concurrently administered with other drugs, including other known anti-PD drugs, in which case the dosage of each agent required to exert a therapeutic effect during combinative therapy may be less than the dosage necessary for monotherapeutic effectiveness. Examples of drugs for concurrent administration include, but are not limited to, L-dopa, carbo-levo, apomorphine, pirebedil, bromocriptine, carbergoline, pramipexole, ropinirole, selegiline, lazabemide, rasagiline, sildenafil citrate (Viagra), caffeine, Mirapex, Naprelan, Oxybutin and aspirin.

The invention further provides uses of PDE5 inhibitors in the manufacture of a medicament for treating PD.

Assays to determine the specific activity of PDE5s are well known in the art and any such assay can be used to identify inhibitors useful in the therapeutic methods disclosed herein. Preferred inhibitors possess desirable physical and biological properties, e.g., a sufficient water solubility, bioavailability, and metabolic stability, for therapeutic use in the treatment of PD.

Anti-PD therapeutically effective amounts of PDE5 inhibitors include amounts effective for slowing or preventing the progression of PD and amounts effective to alleviate or reduce the clinical symptoms of PD. PDE5 inhibitors can be administered to humans at doses ranging from about 0.1 mg to about 1000 mg daily or more preferably at doses ranging from about 1 mg to about 100 mg daily for adults. Even more preferably, doses range from about 2 mg to about 20 mg over a 24 hour period. Most preferable are doses calculated to provide an effective circulating blood level. Equivalent dosing of PDE5 inhibitors can be administered at longer intervals, e.g., larger doses once or twice weekly. The dosage of the drug may be increased or decreased, and the duration of treatment may be shortened or lengthened as determined by the treating physician. The frequency of dosing will depend on the pharmacokinetic parameters of the agents and the route of administration. The optimal pharmaceutical formulation will be determined by one skilled in the art depending upon the route of administration and desired dosage. See for example, Remington's Pharmaceutical Sciences, 18th Ed. (1990, Mack Publishing Co., Easton, Pa. 18042) pages 1435–1712, the disclosure of which is hereby incorporated by reference. Such formulations may influence the physical state, stability, rate of in vivo release, and rate of in vivo clearance of administered agents.

Those of ordinary skill in the art will readily optimize effective dosages and administration regimens as determined by good medical practice and the clinical condition of the individual patient. Regardless of the manner of administration, the specific dose may be calculated according to body weight, body surface area or organ size. Further refinement of the calculations necessary to determine the appropriate dosage for treatment involving each of the above mentioned formulations is routinely made by those of ordinary skill in the art without undue experimentation. Appropriate dosages may be ascertained through use of established assays for determining blood level dosages in conjunction with appropriate doseresponse data. The final dosage regimen will be determined by the attending physician, considering various factors which modify the action of drugs, e.g., the drug's specific activity, the severity of the damage and the responsiveness of the patient, the age, condition, body weight, sex and diet of the patient, the severity of the clinical symptoms, time of administration and other clinical factors.

PDE5 inhibitors may be administered systemically via, e.g., oral, intravenous, intramuscular or subcutaneous routes. The drug may be aerosolized for pulmonary administration, formulated in a spray for nasal administration, administered intraventricularly or intrathecally into the cerebrospinal fluid, or administered intravenously via continuous infusion pump. The drugs may also be administered topically via, e.g., drops (particularly ophthalmic drops), ointment, patch or per rectum via e.g., suppositories or enemas. For the combination treatments, PDE5 inhibitors and another anti-PD agent can be administered simultaneously or sequentially.

While it is possible to administer a compound employed in the methods of this invention directly without any formulation, the compounds are usually administered in the form of pharmaceutical compositions comprising a pharmaceutically acceptable excipient and at least one active ingredient. These compositions can be administered by a variety of routes including oral, buccal, rectal, transdermal, subcutaneous, intravenous, intramuscular, and intranasal. Many of the compounds employed in the methods of this invention are effective as both injectable and oral compositions. Such compositions are prepared in a manner well known in the pharmaceutical art and comprise at least one active compound.

In making the compositions employed in the present invention, the active ingredient usually is mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g., about 40 mesh.

The compositions used in the invention can be formulated to provide quick, sustained, or delayed release of the active ingredient after administration to the patient by employing procedures known in the art.

The compositions preferably are formulated in a unit dosage form. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient. The active compounds generally are effective over a wide dosage range. However, it will be understood that the amount of the compound actually administered will be determined by a physician, in the light of the relevant circumstances.

Numerous additional aspects and advantages of the invention will become apparent to those skilled in the art upon consideration of the following embodiments thereof. Example 1 describes the preparation of PDE5. Example 2 describes an assay for PDE5 activity. Example 3 describes assays to measure the effects of PDE5 inhibitors. Example 4 describes administration of a PDE5 inhibitor compound to a patient suffering from PD.

EXAMPLE 1

Human PDE5 Preparation for Use in Inhibitor Assays

Recombinant production of human PDE5 was carried out essentially as described in Example 7 of U.S. Pat. No. 5,702,936, incorporated herein by reference, except that the yeast transformation vector employed, which is derived from the basic ADH2 plasmid described in V. Price et al., *Methods in Enzymology*, 185, pages 308–318 (1990) incorporated yeast ADH2 promoter and terminator sequences rather than ADH1 promoter and terminator sequences and the *Saccharomyces cerevisiae* host was the protease-deficient strain BJ2-54 deposited on Aug. 31, 1998 with the American Type Culture Collection, Manassas, Va., under accession number ATCC 74465. Transformed host cells were grown in 2×SC-leu medium, pH 6.2, with trace metals, and vitamins. After 24 hours, YEP medium containing glycerol was added to a final concentration of 2×YEP/3% glycerol. Approximately 24 hours later, cells were harvested, washed, and stored at −70° C.

Cell pellets (29 g) were thawed on ice with an equal volume of lysis buffer (25 mM Tris-Cl, pH 8, 5 mM $MgCl_2$, 0.25 mM dithiothreitol, 1 mM benzamidine, and 10 $\mu$M $ZnSO_4$). Cells were lysed in a microfluidizer with $N_2$ at 20,000 psi. The lysate was centrifuged and filtered through 0.45 $\mu$M disposable filters. The filtrate was applied to a 150 ml column of Q Sepharose Fast Flow (Pharmacia). The column was washed with 1.5 volumes of Buffer A (20 mM Bis-Tris Propane, pH 6.8, 1 mM $MgCl_2$, 0.25 mM dithiothreitol, 10 $\mu$M $ZnSO_4$) and eluted with a step gradient of 125 mM NaCl in Buffer A followed by a linear gradient of 125–1000 mM NaCl in Buffer A.

Active fractions from the linear gradient were applied to a 180 ml hydroxylapatite column in Buffer B (20 mM Bis-Tris Propane (pH 6.8), 1 mM $MgCl_2$, 0.25 mM dithiothreitol, 10 $\mu$M $ZnSO_4$, and 250 mM KCl). After loading, the column was washed with 2 volumes of Buffer B and eluted with a linear gradient of 0–125 mM potassium phosphate in Buffer B. Active fractions were pooled, precipitated with 60% ammonium sulfate, and resuspended in Buffer C (20 mM Bis-Tris Propane, pH 6.8, 125 mM NaCl, 0.5 mM dithiothreitol, and 10 µM ZnSO$_4$). The pool was applied to a 140 ml column of Sephacryl S-300 HR and eluted with Buffer C. Active fractions were diluted to 50% glycerol and stored at −20° C. The resultant preparations were about 85% pure by SDS-PAGE.

EXAMPLE 2

Assay for PDE5 Activity

Activity of PDE5 preparations can be measured by standard assays in the art. For example, specific activity of any PDE can be determined as follows. PDE assays utilizing a charcoal separation technique are performed essentially as described in Loughney, et al., *J. Biol. Chem.* 271:796–806 (1996). In this assay, PDE5 activity converts [$^{32}$P]cGMP to [$^{32}$P]5'GMP in proportion to the amount of PDE5 activity present. The [$^{32}$P]5'GMP is then quantitatively converted to free [$^{32}$P] phosphate and unlabeled adenosine by the action of snake venom 5'-nucleotidase. Hence, the amount of [$^{32}$P] phosphate liberated is proportional to enzyme activity. The assay is performed at 30° C. in a 100 µL reaction mixture containing (final concentrations) 40 mM Tris-Cl (pH 8.0), 1 µM ZnSO$_4$, 5 mM MgCl$_2$, and 0.1 mg/ml bovine serum albumin. PDE5 is present in quantities that yield <30% total hydrolysis of substrate (linear assay conditions). The assay is initiated by addition of substrate (1 mM [$^{32}$P]cGMP), and the mixture is incubated for twelve minutes. Seventy-five (75) µg of *Crotalus atrox* venom is then added, and the incubation is continued for three more minutes (fifteen minutes total). The reaction is stopped by addition of 200 µL of activated charcoal (25 mg/ml suspension in 0.1 M NaH$_2$PO$_4$, pH 4). After centrifugation (750×g for three minutes) to sediment the charcoal, a sample of the supernatant is taken for radioactivity determination in a scintillation counter and the PDE5 activity is calculated.

EXAMPLE 3

Assays to Measure the Effects of PDE5 Inhibitors

Effects of inhibitors of the present invention on enzymatic activity of PDE5 preparations can be assessed in either of two assays which differ from each other principally on the basis of scale and provide essentially the same results in terms of IC$_{50}$ values. Both assays involve modification of the procedure of Wells et al., *Biochim. Biophys. Acta*, 384, 430 (1975).

The first of the assays is performed in a total volume of 200 µl containing 50 mM Tris pH 7.5, 3 mM Mg acetate, 1 mM EGTA, 50 µg/ml snake venom nucleotidase and 50 nM [$^3$H]-cGMP (Amersham). Compounds of the invention are dissolved in DMSO finally present at 2% in the assay. The assays are incubated for 30 minutes at 30° C. and stopped by addition of 800 µl of 10 mM Tris pH 7.5, 10 mM EDTA, 10 mM theophylline, 0.1 mM adenosine, and 0.1 mM guanosine. The mixtures are loaded on 0.5 ml QAE Sephadex columns, and eluted by 2 ml of 0.1 M formate (pH 7.4). The eluted radioactivity is measured by scintillation counting in Optiphase Hisafe 3.

A second, microplate PDE assay uses Multiscreen plates and a vacuum manifold. The assay (100 µl) contains 50 mM Tris pH 7.5, 5 mM Mg acetate, 1 mM EGTA and 250 µg/ml snake venom nucleotidase. The other components of the reaction mixture are as described above. At the end of the incubation, the total volume of the assay is loaded on a QAE Sephadex microcolumn plate by filtration. Free radioactivity is eluted with 200 µl of water from which 50 µl aliquots are analyzed by scintillation counting as described above.

EXAMPLE 4

Administration of a PDE5 Inhibitor Compound

A patient who was administered a PDE5 inhibitor of the invention noted an improvement in his Parkinson's symptoms, i.e., a reduction in his symptoms. The PDE5 inhibitor was 5-(2-ethoxy-5-(4-methyl-1-piperazinylsulphonyl)phenyl)-1-methyl-3-n-propyl-1,6-dihydro-7H-pyrazolo[4,3-d]pyrimidin-7-one, otherwise known as sildenafil citrate (Viagra®).

Numerous modifications and variations in the practice of the invention are expected to occur to those skilled in the art upon consideration of the foregoing detailed description of the presently preferred embodiments thereof. Consequently, the only limitations which should be placed upon the scope of the present invention are those which appear in the appended claims.

I claim:

1. A method of treating Parkinson's Disease comprising administering a therapeutically effective amount of a compound that inhibits cGMP-specific phosphodiesterase (PDE5).

2. The method of claim 1 wherein the compound has a structural formula

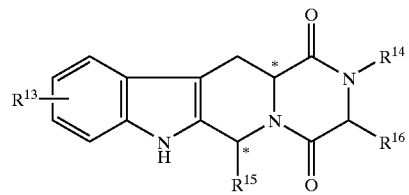

or a salt or solvate thereof, wherein R$^{13}$ is selected from the group consisting of hydra, halo, and C$_{1-6}$alkyl;

R$^{14}$ is selected from the group consisting of hydro, C$_{1-6}$alkyl, C$_{2-6}$alkenyl, C$_{2-6}$alkynyl, halo, C$_{3-8}$cycloalkyl, C$_{3-8}$cycloalkylC$_{1-3}$alkyl, and arylC$_{1-3}$alkyl, wherein aryl is phenyl or phenyl substituted with one to three substituents independently selected from the group consisting of halo, C$_{1-6}$alkyl, C$_{1-6}$alkoxy, and methylenedioxy, and heteroarylC$_{1-3}$alkyl, wherein heteroaryl is thienyl, furyl, or pyridyl, each optionally substituted with one to three substituents independently selected from the group consisting of halo, C$_{1-6}$alkyl, and C$_{1-6}$alkoxy, R$^{15}$ represents an optionally substituted monocyclic aromatic ring selected from the group consisting of benzene, thiophene, furan, and pyridine, or an optionally substituted bicyclic ring

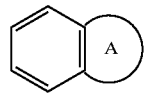

attached to the rest of the molecule via one of the benzene ring carbon atoms, wherein the fused ring A is a 5- or 6-membered ring, saturated or partially or fully unsaturated, and comprises carbon atoms and optionally one or two heteroatoms selected from oxygen, sulphur, and nitrogen; and $R^{16}$ represents hydro or $C_{1-3}$alkyl, or $R^{14}$ and $R^{16}$ together represent a 3- or 4-membered alkyl or alkenyl chain component of a 5- or 6-membered ring.

3. The method of claim 2 wherein $R^{14}$ is hydro or $C_{1-6}$alkyl; $R^{15}$ is the bicyclic ring

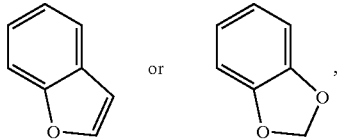

optionally substituted with one or more groups independently selected from halo and $C_{1-3}$alkyl; and $R^{16}$ is hydro or $C_{1-3}$alkyl.

4. The method of claim 2 wherein the compound is selected from the group consisting of (6R, 12aR)-2,3,6,7,12,12a-hexahydro-6-(5-benzofuranyl)-2-methylpyrazino[2',1':6,1]pyrido[3,4-b]indole-1,4-dione;

(6R, 12aR)-2,3,6,7,12,12a-hexahydro-6-(5-benzofuranyl)-pyrazino[2',1':6,1]pyrido[3,4-b] indole-1,4-dione;

(3S, 6R, 12aR)-2,3,6,7,12,12a-hexahydro-6-(5-benzofuranyl)-3-methylpyrazino[2',1':6,1]pyrido[3,4-b]-indole-1,4-dione;

(3S, 6R,12aR)-2,3,6,7,12,12a-hexahydro-6-(5-benzofuranyl)-2,3-dimethylpyrazino[2',1':6,1]pyrido[3,4-b]indole-1,4-dione;

(6R, 12aR)-2,3,6,7,12,12a-hexahydro-6-(5-benzofuranyl)-2-isopropylpyrazino[2',1':6,1]pyrido[3,4-b]indole-1,4-dione;

a physiologically acceptable salt or solvate thereof; and mixtures thereof.

5. The method of claim 2 wherein the compound is (6R, 12aR)-2,3,6,7,12,12a-hexahydro-6-(5-benzofuranyl)-2-methylpyrazino[2',1':6,1]pyrido[3,4-b]-indole-1,4-dione.

6. The method of claim 1 wherein the compound as a structural formula

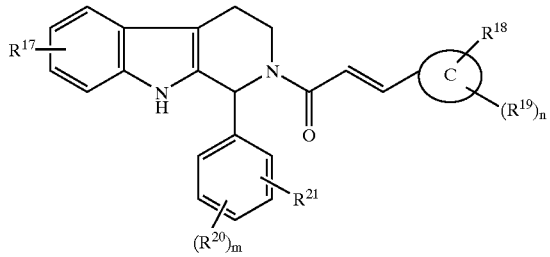

or a salt or solvate thereof, wherein ring C represents a 5- or 6-membered heteroaryl group containing at least one heteroatom selected from the group consisting of oxygen, nitrogen, and sulfur;

$R^{17}$ represents hydro or halo;

$R^{18}$ is selected from the group consisting of hydro, nitro, trifluoromethyl, trifluoromethoxy, halo, cyano, a 5- or 6-membered heterocyclic group containing at least one heteroatom selected from the group consisting of oxygen, nitrogen, and sulfur, optionally substituted with $C(=O)OR^a$ or $C_{1-4}$alkyl, $C_{1-6}$alkyl, optionally substituted with $OR^h$, $C_{1-3}$alkoxy, $C(=O)R^h$, $OC(=O)OR^h$, $C(=O)OR^h$, $C_{1-4}$alkyleneHet, $C_{1-4}$alkyleneC(=O)OR^h$, $OC_{1-4}$alkyleneC(=O)OR^h$, $C_{1-4}$alkyleneOC_{1-4}alkyleneC(=O)OR^h$, $C(=O) NR^iSO_2R^j$, $C(=O) C_{1-4}$alkyleneHet, $C_{1-4}$alkyleneNR^hR^i$, $C_{2-6}$alkenyleneNR^hR^i$, $C(=O) NR^hR^i$, $C(=O) NR^hR^j$, $C(=O) NR^hC_{1-4}$alkyleneOR^i$, $C(=O) NR^hC_{1-4}$alkyleneHet, $OR^i$, $OC_{2-4}$alkyleneNR^hR^i$, $OC_{1-4}$alkyleneCH(OR^h)CH_2NR^hR^i$, $OC_{1-4}$alkyleneHet, $OC_{2-4}$alkyleneOR^h$, $OC_{2-4}$alkyleneNR^hC(=O)OR^i$, $NR^hR^i$, $NR^hC_{1-4}$alkyleneNR^hR^i$, $NR^hC(=O)R^i$, $NR^hC(=O)NR^hR^i$, $N(SO_2C_{1-4}alkyl)_2$, $NR^h(SO_2C_{1-4}alkyl)$, $SO_2NR^hR^i$, and $OSO_2$trifluoromethyl;

$R^{19}$ is selected from the group consisting of hydro, halo, $OR^h$, $C_{1-6}$alkyl, nitro, and $NR^hR^i$;

or $R^{18}$ and $R^{19}$ are taken together to form a 3- or 4-membered alkylene or alkenylene chain component of a 5- or 6-membered ring, optionally containing at least one heteroatom;

$R^{20}$ is selected from the group consisting of hydro, halo, nitro, trifluoromethoxy, $C_{1-6}$alkyl, $OC_{1-6}$alkyl, and $C(=O)O^h$;

$R^{21}$ is hydro;

or $R^{20}$ and $R^{21}$ are taken together to form a 3- or 4-membered alkylene or alkenylene chain component of a 5- or 6-membered ring, optionally containing at least one heteroatom;

Het represents a 5- or 6-membered heterocyclic group containing at least one heteroatom selected from the group consisting of oxygen, nitrogen, and sulfur, and is optionally substituted with $C_{1-4}$alkyl;

$R^h$ and $R^i$, the same or different, are independently selected from hydro and $C_{1-6}$alkyl;

$R^j$ represents phenyl or $C_{4-6}$cycloalkyl, wherein the phenyl or $C_{4-6}$cycloalkyl group can be optionally substituted with one or more halo atoms, one or more $C(=O)OR^a$, or one or more $OR^h$;

n is an integer 1, 2, or 3; and m is an integer 1 or 2.

7. The method of claim 6 wherein ring C is a heteroaryl group containing at least one nitrogen or sulfur atom, $R^{19}$ is hydro, and $R^{18}$ is selected from the group consisting of $NR^hR^i$ and a 5- or 6-membered heterocyclic group containing at least one nitrogen optionally substituted with $C_{1-4}$alkyl.

8. The method of claim 1 wherein the compound has a structural formula

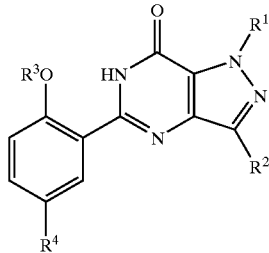

wherein $R^1$ is methyl or ethyl; $R^2$ is n-propyl; $R^3$ is ethyl, n-propyl, or allyl; $R^4$ is $COCH_2NR^5R^6$, $CONR^5R^6$, $SO_2NR^9R^{10}$, or 1-methyl-2-imidazolyl; $R^5$ and $R^6$ together represent, with the nitrogen atom to which they are attached, a morpholino or 4-N($R^{11}$)-piperazinyl group; $R^9$ and $R^{10}$ together with the nitrogen atom to which they are attached represent a 4-N($R^{12}$)-piperazinyl group; $R^{11}$ is methyl or acetyl; and $R^{12}$ is hydro, methyl, 2-propyl, or 2-hydroxyethyl.

9. The method of claim 8 wherein the compound is selected from the group consisting of 5-(2-ethoxy-5-morpholinoacetylphenyl)-1-methyl-3-n-propyl-1,6-dihydro-7H-pyrazolo[4,3-d]pyrimidin-7-one;

5-(5-morpholinoacetyl-2-n-propoxyphenyl)-1-methyl-3-n-propyl-1,6-dihydro-7H-pyrazolo[4,3-d]pyrimidin-7-one;

5-(2-ethoxy-5-(4-methyl-1-piperazinylsulphonyl)phenyl)-1-methyl-3-n-propyl-1,6-dihydro-7H-pyrazolo[4,3-d]-pyrimidin-7-one;

5-(2-allyloxy-5-(4-methyl-1-piperazinylsulphonyl)-phenyl)-1-methyl-3-n-propyl-1,6-dihydro-7H-pyrazolo-[4,3-d]pyrimidin-7-one;

5-(2-ethoxy-5-[4-(2-propyl)-1-piperazinylsulphonyl]-phenyl)-1-methyl-3-n-propyl-1,6-dihydro-7H-pyrazolo-[4,3-d]pyrimidin-7-one;

5-(2-ethoxy-5-[4-(2-hydroxyethyl)-1-piperazinylsulphonyl]phenyl)-1-methyl-3-n-propyl-1,6-dihydro-7H-pyrazolo-[4,3-d]pyrimidin-7-one;

5-(5-[4-(2-hydroxyethyl)-1-piperazinylsulphonyl]-2-n-propoxyphenyl)-1-methyl-3-n-propyl-1,6-dihydro-7H-pyrazolo[4,3-d]pyrimidin-7-one;

5-(2-ethoxy-5-(4-methyl-1-piperazinylcarbonyl)phenyl)-1-methyl-3-n-propyl-1,6-dihydro-7H-pyrazolo[4,3-d]-pyrimidin-7-one;

5-(2-ethoxy-5-(1-methyl-2-imidazolyl)phenyl)-1-methyl-3-n-propyl-1,6-dihydro-7H-pyrazolo[4,3-d]pyrimidin-7-one;

and mixtures thereof.

10. The method of claim 9 wherein the compound is 5-(2-ethoxy-5-(4-methyl-1-piperazinylsulphonyl)phenyl)-1-methyl-3-n-propyl-1,6-dihydro-7H-pyrazolo[4,3-d]pyrimidin-7-one.

11. The method of claim 1 wherein the compound is administered orally.

12. The method of claim 1 further comprising administering a second drug useful in treatment of Parkinson's Disease.

13. The method of claim 12 wherein the second drug is selected from the group consisting of L-dopa, carbo-levo, apomorphine, pirebedil, bromocriptine, carbergoline, pramipexole, ropinirole, selegiline, lazabemide, rasagiline, caffeine, naproxen, Oxybutin, aspirin, and mixtures thereof.

14. The method of claim 13 wherein the compound and second drug are administered simultaneously.

15. The method of claim 13 wherein the compound and second drug are administered sequentially.

* * * * *

UNITED STATES PATENT AND TRADEMARK OFFICE
CERTIFICATE OF CORRECTION

PATENT NO.    : 6,492,371 B2
DATED         : December 10, 2002
INVENTOR(S)   : H.H. Roylance It is certified that error appears in the above-identified patent and that said Letters Patent is hereby corrected as shown below:

Column 1,
Line 46, "instead" should be -- Instead --

Column 3,
Line 10, "(CAMP)" should be -- (cAMP) --

Column 4,
Lines 34, 36 and 37, "PDEIc" should be -- PDE1c --

Column 7,
Line 38, "C(=O) NR'SO$_2$R$^j$" should be -- C(=O) NR$^i$SO$_2$R$^j$ --

Column 9,
Line 20, "doseresponse" should be -- dose-response --

Column 12,
Line 44, "hydra" should be -- hydro --
Line 47, "C$_{3-8}$cycloalkylC$_{1-3}$aikyl" should be -- C$_{3-8}$cycloalkylC$_{1-3}$alkyl --

Signed and Sealed this

Thirteenth Day of April, 2004

JON W. DUDAS
*Acting Director of the United States Patent and Trademark Office*